(12) United States Patent
Wen

(10) Patent No.: US 8,382,714 B2
(45) Date of Patent: Feb. 26, 2013

(54) RAIL-GUIDED EPIDURAL-SPINAL NEEDLE

(76) Inventor: Yihui Wen, Pingyang County (CN)

( * ) Notice: Subject to any disclaimer, the term of this patent is extended or adjusted under 35 U.S.C. 154(b) by 0 days.

(21) Appl. No.: 13/112,181

(22) Filed: May 20, 2011

(65) Prior Publication Data

US 2011/0230846 A1 Sep. 22, 2011

Related U.S. Application Data

(63) Continuation-in-part of application No. 12/300,167, filed as application No. PCT/CN2007/001541 on May 11, 2007.

(30) Foreign Application Priority Data

May 12, 2006 (CN) ...................... 2006 2 0115262 U

(51) Int. Cl.
*A61M 5/178* (2006.01)
(52) U.S. Cl. ........ 604/161; 604/160; 604/510; 604/272; 604/273; 604/274
(58) Field of Classification Search .......... 604/272–274, 604/161, 160, 510
See application file for complete search history.

(56) References Cited

U.S. PATENT DOCUMENTS

| | | |
|---|---|---|
| 3,469,580 A | 9/1969 | Huddy |
| 4,808,157 A | 2/1989 | Coombs |
| 4,958,901 A * | 9/1990 | Coombs .......................... 604/44 |
| 5,213,578 A | 5/1993 | Heiliger et al. |
| 5,478,328 A * | 12/1995 | Silverman et al. ............ 604/272 |
| 6,004,293 A | 12/1999 | Bell |
| 2005/0203465 A1 | 9/2005 | Llurba |

FOREIGN PATENT DOCUMENTS

| | | |
|---|---|---|
| CN | 2103319 U | 5/1992 |
| CN | 2380189 Y | 5/2000 |
| CN | 2618569 Y | 6/2004 |
| DE | 20018216 U1 | 2/2002 |
| EP | 0872215 A2 | 10/1998 |
| GB | 904237 A | 8/1962 |
| JP | 2503997 T | 11/1990 |
| JP | 2614508 | 5/1997 |
| WO | WO-0147591 A1 | 7/2001 |

* cited by examiner

*Primary Examiner* — Bhisma Mehta
*Assistant Examiner* — Edelmira Bosques
(74) *Attorney, Agent, or Firm* — Rabin & Berdo, P.C.

(57) ABSTRACT

A rail-guided epidural-spinal needle, which includes an epidural needle including a base and a needle shaft connected to the base, the needle shaft having a groove that is formed on an outer surface of the needle shaft and extends along an axis of the needle shaft, the base having an elevated spinal needle inlet disposed thereon, the spinal needle inlet having a conduit formed therein, the conduit being of an acute angle with the groove in a side view of the epidural needle, and being in alignment with the groove in a top view of the epidural needle. The rail-guided epidural-spinal needle also includes a spinal needle having a tip with a unilaterally curved conformation down one side, such that, when the spinal needle is inserted into the conduit of the spinal needle inlet, and pushed forward, the tip thereof reaches the groove and slides along the groove.

3 Claims, 5 Drawing Sheets

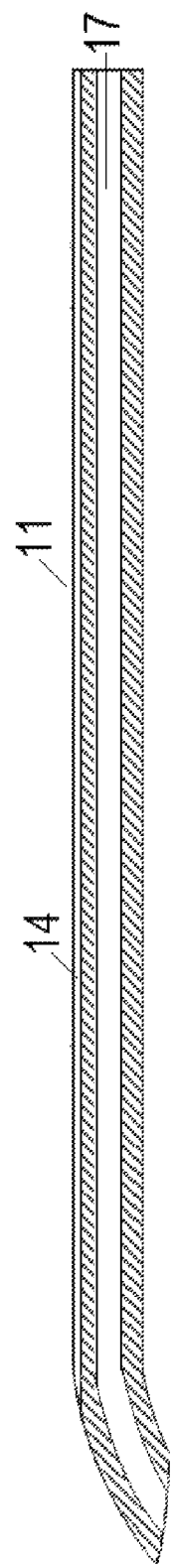

RAIL-GUIDED EPIDURAL-SPINAL NEEDLE

CROSS-REFERENCE TO RELATED APPLICATIONS

This application is a continuation-in-part application of U.S. application Ser. No. 12/300,167, which was filed on Nov. 10, 2008 and was the National Stage of International Application No. PCT/CN2007/001541, filed on May 11, 2007, which in turn claimed the priority of Chinese Application No. 200620115262.3, filed on May 12, 2006.

BACKGROUND

1. Technical Field

The present invention relates to an epidural-spinal needle. More specifically, it relates to a rail-guided puncture needle for combined epidural-spinal anesthesia.

2. Background Information

Puncture anesthesia is used in a variety of medical and surgical procedures. In a typical puncture anesthesia process, an epidural needle is first punctured into an epidural space, a spinal needle, guided by an inner lumen of the epidural needle, is then inserted to pierce the spine dura mater and the arachnoids mater associated to the epidural space to arrive at the subarachnoid space. An anesthetic agent may then be administrated into subarachnoid space through the spinal needle. After the spinal needle is withdrawn, an epidural catheter can be threaded into epidural space through the inner lumen of the epidural needle, so that continuous epidural anesthesia can be applied via the epidural catheter. Finally, the epidural needle is removed to complete the anesthesia puncture process.

A conventional epidural needle has a lumen formed therein. The spinal needle is inserted into the lumen, and the tip of the spinal needle passes through the lumen to pierce the spine dura mater and the arachnoids mater into subarachnoid space. After the spinal needle is withdrawn from the lumen, the epidural catheter is disposed into epidural space through the same lumen.

SUMMARY

A rail-guided epidural-spinal needle, which includes an epidural needle including a base and a needle shaft connected to the base, the needle shaft having a groove that is formed on an outer surface of the needle shaft and extends along an axis of the needle shaft, the base having an elevated spinal needle inlet disposed thereon, the spinal needle inlet having a conduit formed therein, the conduit being of an acute angle with the groove in a side view of the epidural needle, and being in alignment with the groove in a top view of the epidural needle. The rail-guided epidural-spinal needle also includes a spinal needle having a tip with a unilaterally curved conformation down one side (that is, a beaked structure), such that, when the spinal needle is inserted into the spinal needle inlet and the conduit and pushed forward, the tip thereof reaches the groove and slides along the groove.

BRIEF DESCRIPTION OF DRAWINGS

FIG. 5 is a sectional view of the needle shaft along the axis of the needle shaft.

DETAILED DESCRIPTION

The invention will now be described in more detail by way of example with reference to the embodiments shown in the accompanying Figures. It should be kept in mind that the following described embodiments are only presented by way of example and should not be construed as limiting the inventive concept to any particular physical configuration. Further, if used and unless otherwise stated, the terms "upper," "lower," "front," "back," "over," "under," and similar such terms are not to be construed as limiting the invention to a particular orientation. Instead, these terms are used only on a relative basis.

Figure 1:
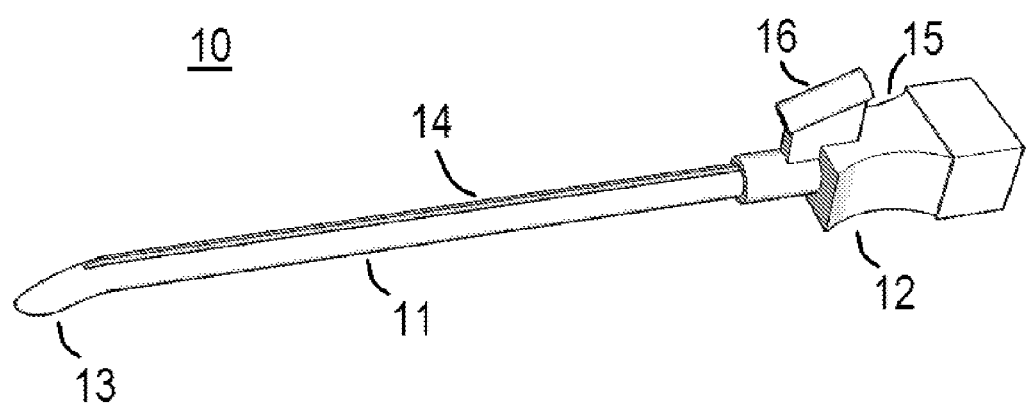
FIG. 1 illustrates the epidural needle in one embodiment of the invention.
Figure 2A:
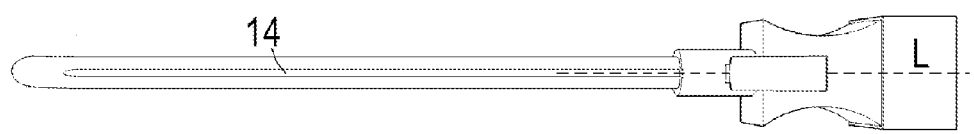
FIGS. 2A-2C respectively show a top view, a bottom view and a side view of the epidural needle in FIG. 1.
Figure 2B:
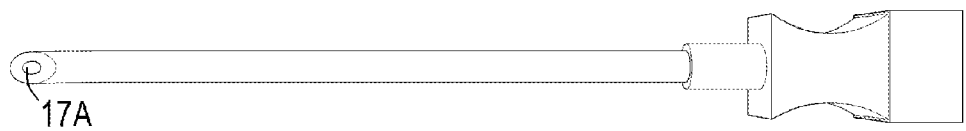
Figure 2C:
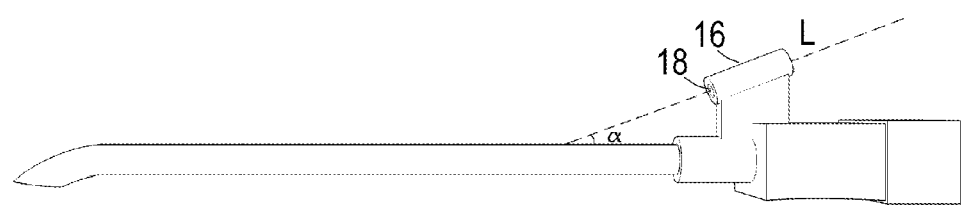

The epidural needle in one embodiment of the invention is illustrated in FIG. 1. FIGS. 2A-2C respectively show a top view, a bottom view and a side view of the epidural needle. As illustrated in FIG. 1, the epidural needle 10 includes a needle shaft 11 and a hub 12. One end of the needle shaft 11 constitutes the tip 13 of the epidural needle 10, and the other end of the needle shaft 11 is connected to the hub 12. The tip 13 of the epidural needle 10 bends slightly downwards, as in a conventional epidural needle. Any type of epidural needle tips that may be contemplated by a person of ordinary skill in the art may be used here. A groove 14 is formed on the outer surface of the needle shaft 11 in parallel to the axis of the cylindrical portion of the needle shaft 11. The groove 14 functions as a rail to guide the spinal needle 20 (shown in FIG. 3) when the spinal needle 20 is used with the epidural needle 10, as described below.

The hub 12 of the epidural needle 10 includes a base 15 in connection with the needle shaft 11, and an elevated spinal needle inlet 16 disposed on the base 15. Although the surfaces of the base 15 in the embodiment illustrated in FIG. 1 are smooth, the base 15 in alternative embodiments may have rugged surfaces or patterned surfaces to facilitate the handling of the epidural needle 10. As illustrated in FIG. 2C, the spinal needle inlet 16 has a conduit 18 through which a spinal needle 20 (shown in FIG. 3) can be inserted (as shown in FIGS. 4A and 4B). The dashed line L represents the path of a point on the tip 23 (shown in FIG. 3) of the spinal needle 20, when the spinal needle 20 is inserted through the conduit 18. An acute angle α is formed between L and the groove 14, as shown in FIG. 2C. As also illustrated in FIG. 2A, the path L, in a top view, is in alignment with the groove 14. In one embodiment of the invention, the conduit 18 does not intersect with the groove 14, so as to allow the movement of the tip 23 of the spinal needle 20 along the groove 14 when the spinal need 20, moving through the conduit 18, reaches the groove 14.

Figure 3:
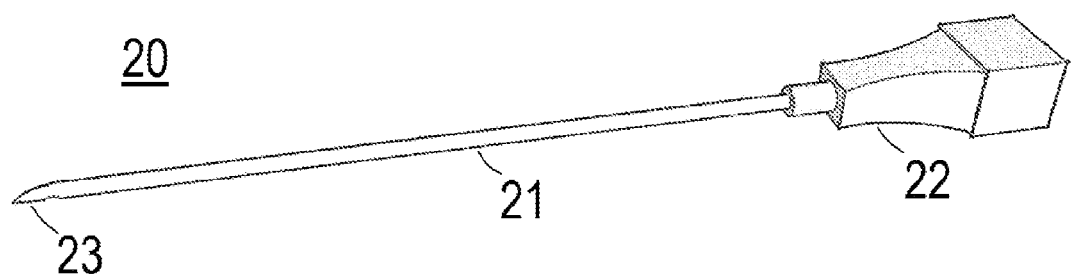
FIG. 3 illustrates the spinal needle in one embodiment of the invention.
Figure 4A:
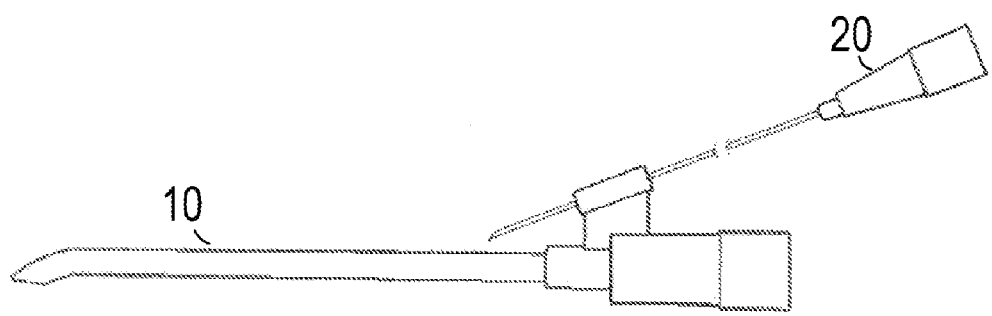
FIGS. 4A and 4B illustrate steps of a typical puncture anesthesia process using the epidural-spinal needle in one embodiment of the invention.
Figure 4B:
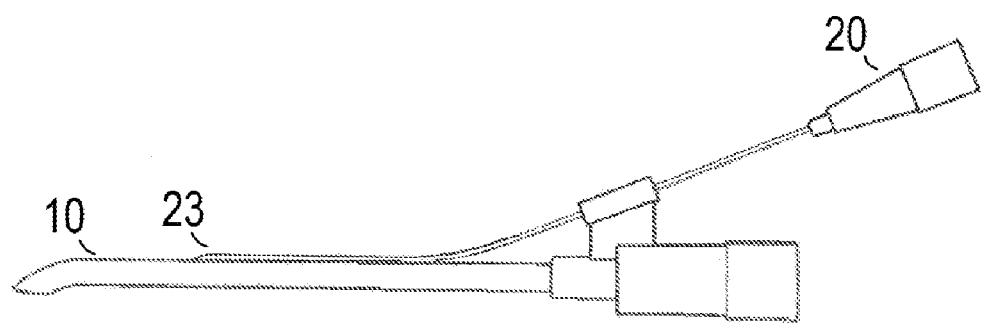

The spinal needle in one embodiment of the invention is illustrated in FIG. 3. The spinal needle 20 includes a needle body 21 and a needle handle 22. One end of the needle body 21 is connected to the needle handle 22, and the other end of the needle body 21 constitutes the tip 23 of the spinal needle 20. As illustrated in FIGS. 4A and 4B, the spinal needle 20 may be inserted into the groove 14 via the conduit 18, and subsequently slides along the groove 14. The tip 23 of the spinal needle 20 has a unilaterally curved conformation down one side (that is, a beaked structure), so that when the spinal needle 20 slides along the groove 14, the foremost portion of the tip 23 of the spinal needle 20 remains in the groove 14, so as to avoid the accidental derailment of the spinal needle 20 from the groove 14. The surfaces of the needle handle 22 in the embodiment illustrated in FIG. 3 are smooth, but in alternative embodiments they may be rugged or patterned to facilitate the handling of the spinal needle 20.

The epidural needle 10 has a lumen 17 (see FIG. 5) formed therein along the axis of the needle shaft 11. The lumen 17 is separated from the groove 14 and is not in communication with the groove 14, as a sectional view shows in FIG. 5. The lumen 17 has a relatively large gauge to permit better assessment of loss of resistance and the passage of an epidural catheter and liquid medicine. The bottom view of the epidural needle 10, illustrated in FIG. 2B, shows an orifice 17A of the lumen 17. The spinal needle 20 also has a lumen (not shown) formed therein to allow the administration of the anesthetic agent.

FIGS. 4A and 4B illustrate steps of a typical puncture anesthesia process using the epidural-spinal needle in one embodiment of the invention. The epidural needle 10 is first punctured into the epidural space, and an epidural catheter (not shown) is placed into the epidural space through the lumen 17 of the epidural needle 10. Next, the spinal needle 20 is inserted into the conduit 18 of the spinal needle inlet 16, as shown in FIG. 4A. The spinal needle 20 is pushed forward until its tip 23 reaches the groove 14 of the epidural needle 10. The spinal needle 20 is then pushed forward further so as to slide along the groove 14, as shown in FIG. 4B. Since an acute angle a is formed between L and the groove 14, so that when the spinal needle 20 is pushed forward, it is also pressed downward towards the bottom of the groove 14, and also because the tip 23 of the spinal needle 20 has a unilaterally curved conformation down one side (that is, a beaked structure), so that the foremost portion of the tip 23 of the spinal needle 20 remains in the groove 14 when sliding forward, the spinal needle 20 slides along the groove 14 until it arrives at the epidural space. Then the tip of the spinal needle 20 pierces the spine dura mater and the arachnoids mater into the subarachnoid space, and anesthetic agent is injected through the spinal needle 20 into the subarachnoid space. Afterwards, the spinal needle 20 and the epidural needle 10 are in turn withdrawn.

By using the epidural-spinal needle of the invention, firstly, the epidural catheter can be disposed in place through the lumen of the epidural needle, and then the spinal needle is guided by the groove into the subarachnoid space, so as to avoid the problem of conventional techniques, in which spinal needle is inserted into the subarachnoid space to administer the anesthetic agent through the inner lumen of epidural needle firstly, and then epidural catheter is placed in the epidural space through the inner lumen of epidural needle after the spinal needle being withdrawn. As such, it also prevents the epidural catheter from being inserted into the subarachnoid space through the needle hole of the spinal needle.

It should be understood, that the invention is not necessarily limited to the specific process, arrangement, materials and components shown and described above, but may be susceptible to numerous variations within the scope of the invention.

What is claimed is:

1. A rail-guided epidural-spinal needle, comprising:
an epidural needle having a lumen formed therein extending along an axis of the epidural needle, the epidural needle including a base and a needle shaft connected to the base, the needle shaft having a groove that is formed on an outer surface of the needle shaft and extends along an axis of the needle shaft, the groove being separate from the lumen, the base having an elevated spinal needle inlet disposed thereon, the spinal needle inlet having a conduit formed therein, the conduit being of an acute angle with the groove in a side view of the epidural needle, and being in alignment with the groove in a top view of the epidural needle; and
a spinal needle having a tip, such that, when the spinal needle is inserted into the conduit of the spinal needle inlet and pushed forward, the tip thereof reaches the groove and slides along the groove.

2. The epidural-spinal needle of claim 1, wherein the tip of the spinal needle has a unilaterally curved conformation down one side, so that when the spinal needle slides along the groove, the foremost portion of the tip remains in the groove, so as to avoid accidental derailment of the spinal needle from the groove.

3. The epidural-spinal needle of claim 1, wherein the conduit does not intersect with the groove.

* * * * *